United States Patent [19]

Ben-Amoz

[11] Patent Number: 4,866,050
[45] Date of Patent: Sep. 12, 1989

[54] ULTRASONIC TRANSDERMAL APPLICATION OF STEROID COMPOSITIONS

[76] Inventor: Daniel Ben-Amoz, 226 Murray Dr., Allentown, Pa. 18104

[21] Appl. No.: 186,815

[22] Filed: Apr. 27, 1988

[51] Int. Cl.$^4$ ............................................. A61K 31/56
[52] U.S. Cl. .................................... 514/179; 514/180
[58] Field of Search ................................ 514/179, 180

[56] References Cited

U.S. PATENT DOCUMENTS

| | | | |
|---|---|---|---|
| 3,007,923 | 11/1961 | Muller et al. | 540/340 |
| 3,962,430 | 6/1976 | O'Neill | 514/179 |
| 4,440,777 | 4/1984 | Zupan | 424/274 |
| 4,482,539 | 11/1984 | Sandweiss et al. | 424/81 |
| 4,701,451 | 10/1987 | Annen et al. | 514/180 |
| 4,710,497 | 12/1981 | Heller et al. | 514/221 |

Primary Examiner—Douglas W. Robinson
Assistant Examiner—Joseph A. Lipovsky
Attorney, Agent, or Firm—Steele, Gould & Fried

[57] ABSTRACT

A dexamethasone delivery composition includes dexamethasone disposed in a cellulosic gel, preferably a hydroxycellulose gel. Lidocaine solubilizes the dexamethasone into the gel to provide a dexamethasone composition of increased concentration and enhanced tissue penetration capability. A method for the transdermal delivery of dexamethasone includes the step of applying the dexamethasone gel composition of the invention to the tissue of a patient and applying ultrasound at the site to effect penetration of the dexamethasone.

7 Claims, No Drawings

ULTRASONIC TRANSDERMAL APPLICATION OF STEROID COMPOSITIONS

BACKGROUND OF THE INVENTION

1. Field of the Invention

This invention relates generally to drug delivery systems and methods, and more particularly to tissue penetrating drug delivery compositions.

2. Description of the Prior Art

Traditional systems for the delivery of drugs and other agents into the body each pose particular problems to the proper administration of the drug or agent. Oral administration subjects the drug or agent to the acidic environment of the stomach, where the drug or agent sometimes is chemically degraded. Enzymes in the gastrointestinal tract, surrounding tissue, or in the liver can destroy much of the drug before it enters the systemic circulation. Some drugs, although able to withstand the destructive environment of the gastrointestinal tract, are nonetheless poorly absorbed through the gastrointestinal tract. High doses of a drug must often be utilized when given orally in order to achieve a desired local concentration.

Hypodermic injection and intraveneous infusion can cause infection and bruising. Controlled release of the drug over a period of time is generally not possible with this form of administration.

Rectal administration is usually accomplished through solid or semi-solid suppositories. These suppositories dispose the drug or agent in a base composition which melts gradually at body temperatures to release the drug or agent. The base composition, however, must usually be kept at low temperatures before use to preserve a fixed shape for proper insertion into the body. The base composition, when melted in the body, can form a film on the surrounding membrane of the body to suppress the desired absorption of the drug or agent into the body. The suppository is discomforting to patients, is difficult to insert, and sometimes is excreted in the original state so that little or none of the drug or agent will be absorbed by the body.

It is known that some of the problems associated with traditional forms of drug administration can be avoided by the use of administration systems and compositions which aim to pass the drug through the skin or other tissue of the body by intercellular and intracellular diffusion. It is known that diffusion is an effective method of application of drugs and agents to the skin for the treatment of a number of dermal conditions. These conditions include pruritus, acne, herpes simplex, psoriasis, and skin cancer. Transdermal diffusion is also useful for the application of cosmetics and sunblocking agents to insure their retention in the skin. It is further well-known that a number of drugs and agents can be administered through the skin or other body tissues for systemic circulation.

Drug application by tissue penetration is particularly helpful for patients who must receive a drug over prolonged periods of time or who must receive several different drugs. These patients can have difficulty following a proper oral delivery regimen, and repeated injections are very discomforting to most patients. The drug or agent can be more effectively and comfortably administered by the application of dosing devices to the skin as infrequently as once or twice per week.

The skin provides an effective barrier to the passage of most substances including those which might have therapeutic effects. This is particularly so for the outer layer of skin which, in humans and most other warm-blooded animals, provides a most effective barrier to penetration. Other tissues in the body generally are more permeable, although this can depend on the particular nature of the tissue and drug in question. It is known that various substances can enhance the ability of drugs and agents to diffuse through the skin and other tissues. Several of these agents, typically surfactants, have been found to be effective but only after producing irreversible damage to the function or structure of the tissue that has been penetrated.

Dimethylsulfoxide (DMSO) has found to be an effective aid to the penetration of drugs and agents through the tissues for both localized drug administration and for introduction into the general body circulation. DMSO has been found to be a preferable penetration enhancing agent that does not impair the structure and function of tissue to the extent encountered with other penetration-enhancing substances. DMSO does, however, have several undesirable side effects. It causes foul taste and body odor, burning and erythema on the skin, activates latent virus infections within cells, reduces the relucency of the lens cortex and produces teratogenicity and tissue necrosis in animals. DMSO can cause liver damage if used extensively, and has the further disadvantage of penetrating any impurities or contaminants that are present as well as the drug or agent.

Dexamethasone is a steroid that is produced naturally in the body by the adrenal cortex, which steroids are called adrenal cortical steroids or corticoids. Some corticoids have the ability to effect the rate of metabolism of glucose and are therefore referred to by the name glucocorticoids. Glucocorticoids have been found useful in the depression of inflammation associated with arthritis and rheumatic diseases. Glucocorticoids are also useful in the treatment of dermatoses, drug reactions, bronchial asthma, lupus erythematosus, angioneuroedema, as well as in the treatment of leukemia. Examples of glucocorticoids include dexamethasone and betamethasone.

Dexamethasone and its salts are described in U.S. Pat. No. 3,007,923, which is herein incorporated by reference. It is understood that the term dexamethasone as herein applied also related to the base form and the various salts including 21-acetate, 21-phosphate, 21-phosphate disodium, 21-dimethylaminoacetate, 21-dimethyl butylrate, tetrahychoplithalate, etc. The application of dexamethasone, or its homologue betamethasone, by transdermal delivery systems has been impeded by the weak solubility of these compounds in most transdermal delivery compositions. It would be desirable to provide a transdermal delivery composition for dexamethasone and its homologues which would provide sufficient levels of the drug in a controlled form of administration and without the side effects encountered with the use of DMSO and other tissue penetration enhancers.

Transdermal delivery has been aided by the use of ultrasound technology. The ultrasound energy is applied to the transdermal delivery composition over the tissue and assists the diffusion of the composition past the tissue.

It is known that lodocaine can solubilize dexamethasone and other steroids for injectable solutions. These injectable solutions, however, suffer the drawbacks of other injectable solutions, namely bruising, damage by the needle, and discomfort.

U.S. Pat. No. 4,440,777 of Zupan discloses the use of eucalyptol as a transport agent for delivering active bio-affecting agents across the stratum corneum which includes dexamethasone.

U.S. Pat. No. 4,482,539 of Sandweiss et al discloses a cream-like gel formulation of betamethasone dipropionate.

However, the formulation is not suitable for use in sonic delivery systems.

SUMMARY OF THE INVENTION

It is an object of the invention to provide a transdermal drug delivery composition and method for dexamethasone and other related steroids which will deliver increased amounts of the drug.

It is another object of the invention to deliver dexamethasone and other related steroids without the side effects associated with DMSO and other tissue penetration enhancers.

It is still another object of the invention to provide a composition for the transdermal delivery of dexamethasone and related steroids which will deliver controlled amounts of the drug through tissue.

These and other objects are accomplished by a composition and method for transdermal delivery of dexamethasone and related steroids in which the dexamethasone is disposed in a cellulosic gel. Lidocaine solubilizes the dexamethasone to produce a composition which will deliver dexamethasone transdermally in a safe and efficient manner. Lidocaine further is an anesthetic so that it acts to relieve local pain.

The lidocaine of the composition is described in U.S. Pat. No. 2,441,498, which is herein incorporated by reference, is preferably viscous and in the form of lidocaine hydrochloride. Other ingredients which typically have been mixed with lidocaine, such as sodium carboxymethylcellulose, and antiseptics such as methylparaben, and propylparaben, can also be used. The transdermal delivery composition of the invention can also include water and glycerin.

Dexamethasone and related glucocorticoid steroids such as betamethasone and their derivatives are delivered transdermally according to the invention by a method in which a composition of the aforementioned description is applied to the tissue. Ultrasonic energy is applied to the composition to diffuse the dexamethasone into the tissue. The dexamethasone can be delivered in large quantities by this method and without the drawbacks encountered by traditional drug delivery methods or by traditional transdermal delivery compositions and methods.

The concentration of the dexamethasone in the formulation can vary greatly and will be dependent upon many factors e.g. the condition for which it is administered, the surface area to which it is applied, the sound waves employed, the concentration of lidocaine, etc. Generally, the concentration will vary from about 0.05 to about 5%, preferably 0.1 to 2.5% by weight of composition.

The ratio of lidocaine to dexamethasone can vary from 10:1 to 1:10 depending on the solubility of the dexamethasone employed. Preferably the ratio of lidocaine to dexamethasone is 1:8 to 1:1.

The gelling agent is commonly used in an amount of 0.5 to 5.0% by weight of the composition.

DETAILED DESCRIPTION OF THE PREFERRED EMBODIMENTS

The invention provides a composition and method for applying dexamethasone and related compounds transdermally in therapeutic concentrations and without the side effects associated with other transdermal delivery compositions. The dexamethasone is disposed in a cellulosic gel, for example, methylcellulose, ethylcellulose, hydroxycellulose, carboxyalkylcellulose, hydroxyethylcellulose, etc. with lidocaine. The lidocaine solubilizes the dexamethasone to increase the concentration of the drug in the gel as well as providing an anesthetic effect.

The invention is particularly well suited for the transdermal application of dexamethasone. It will be understood, however, that the invention could also be suitable for the delivery of related steroids, and particularly glucocorticoids, such as betamethasone and prednisolone.

Lidocaine is the preferred solubilizing agent, although related compounds could also be useful. The related compounds include bupivacaine, etidocaine, pyrrocaine and mepivacaine. The lidocaine solution presently preferred is a viscous lidocaine solution having a number of other ingredients. The viscous lidocaine solution contains lidocaine hydrochloride (2%), sodium carboxymethylcellulose as the gelling agent, and methylparaben and propylparaben as preservatives. Other lidocaine solutions are possible.

The gel can be selected from several gels suitable for this purpose. A preferred gel is an Aquasonic ultrasound gel manufactured by Parker Labs of Orange, New Jersey.

Other materials can be added to the gel composition of the invention. These can include distilled water, polyhydric alcohols and glycerin.

The particular proportions of ingredients that are useful for the invention can vary according to the particular concentration of the drug and delivery rate that is desired. The qualitative composition of the gel would also likely effect the desired proportions. A presently preferred composition is:

| | |
|---|---|
| Dexamethasone | 0.4% |
| Lidocaine* | 0.1% |
| Distilled water | 14.4% |
| Glycerin U.S.P. | 1.2% |
| Aquasonic TM Ultrasound Gel | 5,000 ml |

*Commercial lidocaine solution containing lidocaine hydrochloride 2%, sodium carboxymethylcellulose, methylparaben and propylparaben.

The composition of the invention is particularly well suited for transdermal application with the assistance of ultrasound technology. The method of the invention would apply the composition of the invention to the tissue through which passage of dexamethasone is desired. Ultrasonic energy is applied to the composition to assist the diffusion of the dexamethasone through the tissue membrane.

The composition and method of the invention produce fewer dilatorius side effects than prior art compositions. The inventive composition and method do not carry large amounts of impurities across the tissue membrane as do traditional transdermal compositions such as DMSO.

This invention can be embodied in other forms without departing from the spirit or essential attributes thereof and accordingly, reference should be made to the following claims, rather than to the foregoing specification, as indicating the scope of the invention.

I claim:

1. A method for the transdermal application of a steroid, comprising the steps of applying to a site on a patient where penetration is desired, a composition comprising a cellulosic gel, a steroid disposed in said gel, and at least one solubilizing agent selected from the group consisting of lidocaine, bupivacaine, etidocaine, pyrrocaine and applying ultrasonic energy to said site, whereby said steroid in said gel is driven through the tissue membrane of said patient.

2. The method of claim 1, wherein the steroid is a glucocorticoid.

3. The method of claim 2, wherein the steroid is dexamethasone or a derivative thereof.

4. The method of claim 3, wherein the gel is a carboxymethylcellulose.

5. The method of claim 4, wherein the composition further comprises distilled water and glycerin.

6. The method of claim 1, wherein said composition comprises about 0.4% dexamethasone, about 0.1% lidocaine, about 1.2% glycerin, the balance being carboxymethylcellulose gel.

7. The method claim 1 wherein said steroid is selected from the group consisting of dexamethasone, betamethasone, prednisolone and the derivatives thereof.

* * * * *